United States Patent
Maestri et al.

(10) Patent No.: US 10,457,650 B2
(45) Date of Patent: *Oct. 29, 2019

(54) TRIAZINE COMPOUNDS AS PHOTOSTABILIZING AGENTS

(71) Applicant: 3V Sigma S.P.A., Milan (IT)

(72) Inventors: Francesco Maestri, Bergamo (IT); Ferruccio Berte', Bergamo (IT)

(73) Assignee: 3V Sigma S.P.A., Milan (IT)

( * ) Notice: Subject to any disclaimer, the term of this patent is extended or adjusted under 35 U.S.C. 154(b) by 8 days.

This patent is subject to a terminal disclaimer.

(21) Appl. No.: 15/658,417

(22) Filed: Jul. 25, 2017

(65) Prior Publication Data

US 2018/0030001 A1   Feb. 1, 2018

(30) Foreign Application Priority Data

Jul. 29, 2016 (IT) ................. 102016803 01

(51) Int. Cl.
| | |
|---|---|
| *C07D 251/70* | (2006.01) |
| *C07D 251/54* | (2006.01) |
| *C08K 5/3492* | (2006.01) |
| *A61K 8/49* | (2006.01) |
| *A61Q 17/04* | (2006.01) |

(52) U.S. Cl.
CPC .......... *C07D 251/70* (2013.01); *A61K 8/4966* (2013.01); *A61Q 17/04* (2013.01); *C07D 251/54* (2013.01); *C08K 5/3492* (2013.01)

(58) Field of Classification Search
None
See application file for complete search history.

(56) References Cited

U.S. PATENT DOCUMENTS 6,193,960 B1 * 2/2001 Metzger ............... A61K 8/4966
424/400

FOREIGN PATENT DOCUMENTS

| | | |
|---|---|---|
| EP | 0570838 A1 | 11/1993 |
| EP | 0818450 A1 | 1/1998 |
| EP | 0821939 A1 | 2/1998 |
| EP | 0838214 A2 | 4/1998 |
| EP | 1721600 A1 | 11/2006 |

OTHER PUBLICATIONS

Search Report and Written Opinion of IT 2016000080301 dated Mar. 30, 2017.

* cited by examiner

*Primary Examiner* — Bethany P Barham
*Assistant Examiner* — Barbara S Frazier
(74) *Attorney, Agent, or Firm* — Silvia Salvadori, P.C.; Silvia Salvadori

(57) ABSTRACT

Disclosed are triazine compounds of formula (I):

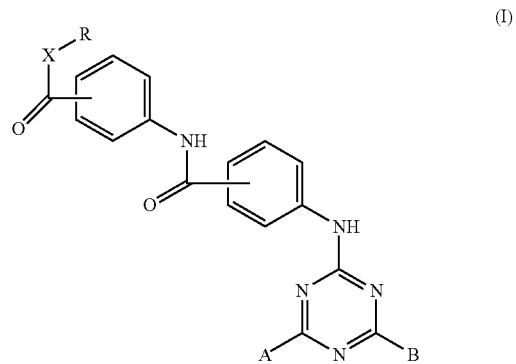

wherein X, R, A and B are as defined in the description as photostabilizing agents against UV-visible radiation.

6 Claims, No Drawings

TRIAZINE COMPOUNDS AS PHOTOSTABILIZING AGENTS

This application claims priority to and the benefit of Italian Application No. 102016000080301 filed Jul. 29, 2016 the content of which is incorporated herein by reference in its entirety.

The present invention relates to s-triazine derivatives, the process for the preparation thereof and their use as light stabilisers.

PRIOR ART

Ultraviolet solar radiation is known to have a damaging effect on skin tissue, and to cause the degradation of polymers. By using particular compounds called sunscreens, which absorb the UV part of solar radiation, harmful effects and aging of the skin and polymer materials can be prevented, or at least slowed.

Numerous substances have been studied and tested as protective agents. A great deal of patent literature exists, relating to compounds belonging to various chemical classes which can absorb in the ultraviolet region, particularly radiation between 290 and 320 nm, called UV-B, which is very harmful.

Relatively few of said compounds have proved suitable for practical application. They include p-methoxycinnamic acid esters, p-dimethylaminobenzoic acid esters, benzotriazoles and hydroxybenzophenones.

A drawback shared by all these compounds is their low ability to absorb radiation between 290 and 320 nm, which means that relatively large quantities are required to obtain the optimum photoprotective effect.

An excellent UV-B absorber should have the following characteristics:

1) High specific extinction $E^1_1$ at 290-320 nm, allowing the use of low doses, resulting in cost savings and minimal toxicological risk
2) Light stability
3) Heat stability
4) Oxidation stability
5) Stability to different pHs
6) Good solubility in the basic substances commonly used for dermatological formulations
7) Negligible toxicity
8) Colour and odour compatible with the intended applications
9) High molecular weight, which reduces the probability of absorption by the skin and increases toxicological safety
10) Compatibility with the various substances generally used in dermatological formulations.

The concentrations of UV-absorber solutions are characterised by the parameter $E^1_1$ (or E11), which corresponds to the specific extinction value measured at the maximum absorption wavelength of a solution containing 1% of the product in question, measured with an optical path of 1 cm.

Numerous derivatives of symmetrical triazine are already known, which can be used in a wide variety of technical applications and sectors due to their properties of absorbing UV rays, in particular UVA and UVB rays. Examples of said triazines are described in DE 3206398, U.S. Pat. Nos. 4,617,390, 4,724,137, 5,233,040, 5,252,323, 5,332,568, IT 1255729, U.S. Pat. Nos. 5,346,691, 5,393,517, EP 832642, U.S. Pat. Nos. 5,744,127, 5,759,525, 5,801,244, 6,018,044, 6,193,960, US 2002085981 and US 2005143577.

In particular, DE 3206398 discloses s-triazine derivatives obtained by reacting trichlorotriazine with p-amino-benzoic acid esters, which absorb intensely in the UV-B region. Unfortunately, the solubility of said compounds in the solvents generally used to formulate sun creams is very low, which makes their practical use problematic and very difficult, especially when the percentage of photoprotector in the composition must be increased to prepare formulations with a high sun protection factor.

IT 1255729 discloses s-triazine derivatives obtained by reacting trichlorotriazine with p-amino-benzoic acid esters or amides with high specific extinction in the UV-B zone and improved solubility in solvents.

EP 832642 discloses s-triazine derivatives obtained by reacting trichlorotriazine with p-aminophenyl-benzoxazole derivatives with high specific extinction in the UV-A zone and improved solubility in solvents.

Sun protection factor (SPF) is a measurement of the photoprotective power of a sunscreen or a cosmetic formulation containing one or more sunscreens. The sun protection factor is the ratio between the MED (Minimal Erythema Dose) determined on protected skin and the MED determined on unprotected skin. It is directly correlated with specific extinction, and therefore also with the amount of photoprotector present in the cosmetic preparation.

DESCRIPTION OF THE INVENTION

It has now been found that the triazine compounds of general formula (I):

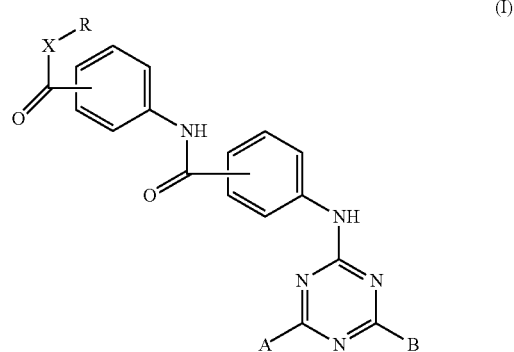

wherein:

X is an —O— or —NH— group

R is a straight, cyclic or branched $C_1$-$C_{18}$ alkyl group and groups A and B can be, independently of one another:

a group of formula (II)

wherein $R_1$ and $R_2$ can be, independently of one another, H, straight, cyclic or branched $C_1$-$C_{22}$ alkyls, $C_1$-$C_{18}$ hydroxyalkyls, $C_2$-$C_{22}$ alkoxyxalkyls or polyalkylene glycols or a group of formula (III)

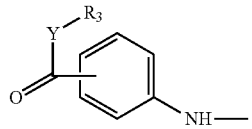
(III)

wherein Y, independently of the value of X, is an —O— or —NH— group
$R_3$ is a straight, cyclic or branched $C_1$-$C_{18}$ alkyl group which is the same or different from R
or a group of formula (IV)

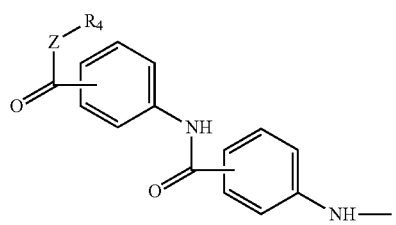
(IV)

wherein Z, independently of the value of X and Y, is an —O— or —NH— group
$R_4$ is a straight, cyclic or branched $C_1$-$C_{18}$ alkyl group which is the same or different from R and $R_3$
not only absorb very intensely in the UV-B region, but also possess excellent solubility in the solvents most commonly used as components of sunscreen formulations, although they have a very high molecular weight, and are therefore more suitable in toxicological terms since they are less likely to be absorbed by the skin tissue.

The invention also relates to the use of said compounds as sunscreens and photostabilisers, due to their ability to perform a surprising skin protection action against the harmful component of solar radiation.

The compounds of the invention can also be usefully employed in the photostabilisation of synthetic polymers to prevent photodegradation and deterioration.

The compounds according to the invention, in addition to high absorption in both the UV-B and the UV-A region, also possess other advantageous characteristics, such as heat stability and lack of toxicity, due to their very high molecular weight.

Typically, the numerical UV-A/UV-B ratio of these compounds, defined as the ratio between the intensity of the radiation absorbed between 320 nm and 400 nm (UVA fraction) and that absorbed between 290 nm and 320 nm (UVB fraction), is greater than 0.20, and preferably greater than 0.30, whereas in the analogous triazine compounds with a 4-aminobenzoate or 4-aminobenzamide substituent different from the substituents described in Formula (IV), it is below about 0.14. Moreover, we have found that by increasing the number of substituents of formula (IV) in the compounds of formula (I), the UV-A light absorption component increases accordingly. The fact that it possesses a significant UV-A component and therefore a broader UV spectrum is undoubtedly an advantage for a substance intended for use as a sunscreen.

DETAILED DESCRIPTION OF THE INVENTION

The invention relates to the triazine compounds of Formula (I):

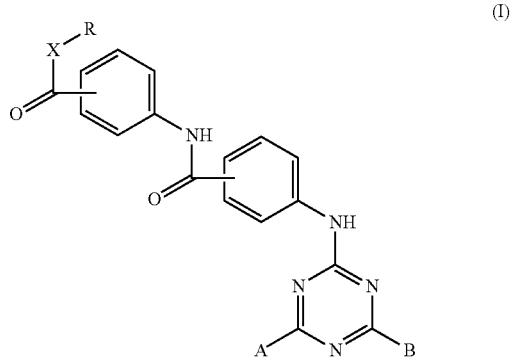
(I)

wherein:
X is an —O— or —NH— group
R is a straight, cyclic or branched $C_1$-$C_{18}$ alkyl group
and groups A and B can be, independently of one another:
a group of formula (II)

(II)

wherein $R_1$ and $R_2$ can be, independently of one another, H, straight, cyclic or branched $C_1$-$C_{22}$ alkyls, $C_1$-$C_{18}$ hydroxyalkyls, $C_2$-$C_{18}$ alkoxyxalkyls or polyalkylene glycols
or a group of formula (III)

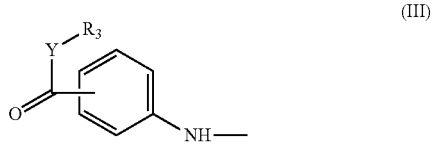
(III)

wherein Y, independently of the value of X, is an —O— or —NH— group
$R_3$ is a straight, cyclic or branched $C_1$-$C_{18}$ alkyl group which is the same or different from R or a group of formula (IV)

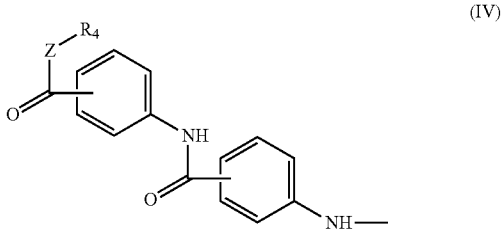
(IV)

wherein Z, independently of the value of X and Y, is an —O— or —NH— group
$R_4$ is a straight, cyclic or branched $C_1$-$C_{18}$ alkyl group which is the same or different from R and $R_3$
as photostabilising agents against UV-visible radiation.

Preferably, in the compounds of formula (I), the carboxylate —CO—O— or amide —CO—NH— (or also —CO—

X—, —CO—Y—, —CO—Z—) groups on the phenyl rings occupy the para or 4 position to the —NH— group, and the R, $R_1$, $R_2$, $R_3$ and $R_4$ groups are straight or branched $C_1$-$C_{12}$ alkyl groups.

Even more preferably, the compounds of formula (I) are the compounds of formulas (V), (VI) and (VII).

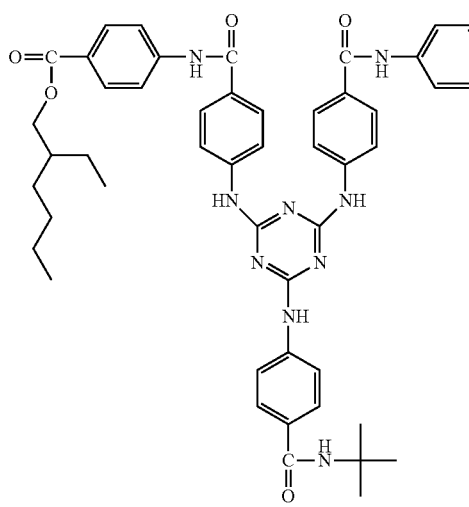

(V)

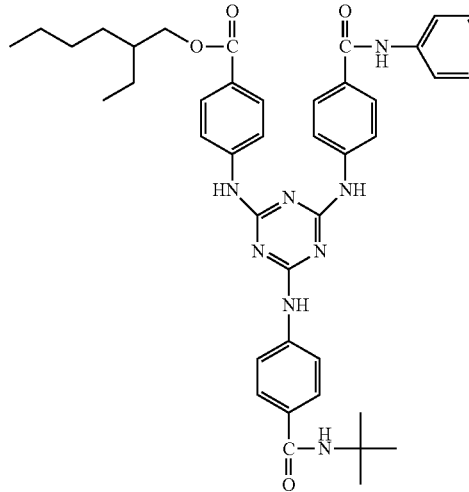

(VI)

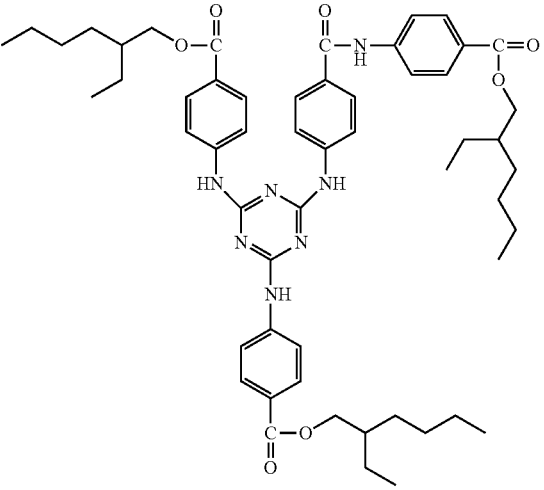

(VII)

The compounds of the invention preferably have a UVA: UVB ratio greater than 0.30.

The compounds of the invention can be prepared by reacting a nitrobenzoyl chloride or bromide with compounds of formula (VIII)

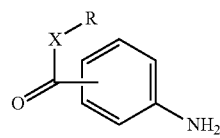

(VIII)

to give the nitro intermediate of formula (IX)

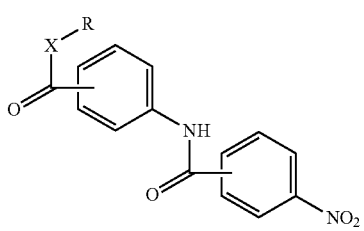

(IX)

which, by subsequent reduction or hydrogenation, affords amino intermediate (X)

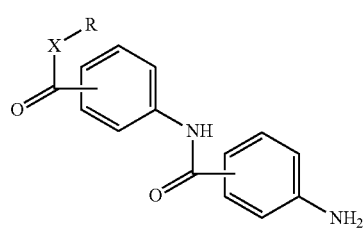

(X)

Intermediate (X) is then reacted with cyanuryl chloride or bromide according to the most suitable stoichiometries and sequences based on well-known synthesis techniques.

The compounds of formula (I) must therefore necessarily be prepared by reacting 1 mole of cyanuryl chloride or bromide with at least 1 mole of intermediate (X), and optionally, where appropriate, with the remaining moles of amino compounds of formula (VIII) and/or (XI), wherein the amines of formula (XI) are:

(XI)

wherein $R_1$ and $R_2$ maintain the meaning described above.

The order in which intermediate (X) and optionally the amines of formulas (VIII) and/or (XI) are reacted with cyanuryl chloride or bromide can follow any intermediate sequence and stoichiometry.

Cyanuryl chloride and bromide have three reactive halogen atoms able to react selectively with ammonia, primary amines and secondary amines at very different temperatures, thus making it possible to replace each halogen atom with the desired amine with quantitative yields.

The subsequent synthesis for the preparation of triazine compounds from amino intermediates such as aminobenzoates and aminobenzamides is well known, and described, for example, in DE 3206398, U.S. Pat. Nos. 4,617,390, 4,724,137, 5,233,040, 5,252,323, 5,332,568, IT 1255729, U.S. Pat. Nos. 5,346,691, 5,393,517, EP 832642, U.S. Pat. Nos. 5,744,127, 5,759,525, 5,801,244, 6,018,044, 6,193,960, US 2002085981, US 2005143577.

As the reaction produces acidity, neutralizing bases are used in many cases, optionally in an aqueous medium, such as sodium hydroxide, sodium carbonate, sodium bicarbonate, calcium hydroxide, calcium carbonate, and tertiary amines such as triethylamine or pyridine.

The solvents wherein the compounds of the invention can be prepared need not be able to dissolve the compounds. However, it is essential that they do not interact chemically with the compounds under the reaction conditions. In this respect they must be inert. Examples of solvents which can be used are saturated linear and branched hydrocarbons such as hexane, cyclohexane, methylcyclohexane, heptane, octane, isooctane, decane, petrols and dearomatised white spirits, aromatic hydrocarbons such as benzene, toluene, xylenes, ethylbenzene and petrols and white spirits also containing aromatic hydrocarbons, ketones such as acetone, methyl ethyl ketone, methyl isobutyl ketone and diisobutyl ketone, ethers such as tetrahydrofuran and dioxane, esters such as ethyl acetate and butyl acetate, and nitriles such as acetonitrile and benzonitrile.

The operating temperatures are from 0° C. to 200° C., preferably from 40 to 150° C. The pressures can range from 0 to 50 bars, preferably from 0 to 5 bars.

The procedure just described is part of the invention.

The compounds of the invention can be advantageously introduced into formulas for cosmetics, either as the only sunscreen or in combination with other known sunscreens.

These formulations constitute a second subject of the invention. Said formulations will preferably contain one or more conventional UVA and UVB sunscreens such as those listed in Annex VII to the European Cosmetics Directive (76/768/EEC) and Annex VI to European Regulation (EC) No. 1223/2009, as amended, in Household and Personal Care, Monographic Special Issue: Skin Care—"The encyclopedia of allowed sunfilters in the world" by Giulio Pirotta, Consultant, via Solferino 4, 21040 Uboldo (VA) Italy and Electronic Code of Federal Regulations (FDA) PART 352—SUNSCREEN DRUG PRODUCTS FOR OVER-THE-COUNTER HUMAN USE; Subpart B—Active Ingredients. Even more preferably, the formulations may contain, in addition to the derivatives according to the invention, one or more sunscreens selected from 2-ethylhexyl p-methoxycinnamate, 2-hydroxy-4-methoxybenzophenone, 2-hydroxy-4-methoxybenzophenone-5-sulphonic acid, ethylhexyl salicylate, ethylhexyl dimethyl PABA, drometrizole trisiloxane, 3-(4'-methylbenzylidene)-d,l-camphor, diethylhexyl butamido triazone, ethylhexyl triazone, 4-(tert-butyl)-4'-methoxy-dibenzoylmethane, 2-cyano-3,3-diphenylacrylic acid 2-ethylhexyl ester, bis-ethylhexyloxyphenol-methoxyphenyl-triazine, methylene-bis-benzotriazolyl-tetramethylbutylphenol, benzoic acid 2-(4-diethylamino-2-hydroxybenzoyl)-hexyl ester, 2,4-bis-[4-[5-(1,1-dimethyl-propyl)benzoxazol-2-yl]phenylimino]-6-[(2-ethylhexyl)imino]-1,3,5-triazine, tris-biphenyltriazine, titanium dioxide and zinc oxide.

The compounds of the invention can also be used already in solution in the solvents allowed by European Regulation (EC) No. 1223/2009 on cosmetic products, as amended.

The compounds of the invention are also suitable for stabilising polymers contained in plastics and coatings against solar and UV radiation. They can therefore be used with other additives as stabilisers, for example to stabilise polyolefins like polyethylene and polypropylene and the copolymers thereof, polyamides, polyesters, polyurethanes and polyvinyl esters.

The invention will be now described in greater detail in the following examples and preparations.

Example 1: Synthesis of 2-ethylhexyl 4-(4-nitrobenzamido) benzoate 77.5 g of a 20 wt % aqueous solution of $Na_2CO_3$, 190.0 g of xylene and 68.5 g of 2-ethylhexyl 4-aminobenzoate are loaded into a 1 liter flask equipped with mechanical stirrer, thermometer, reflux condenser and dropping funnel. Keeping the mixture stirred at 65° C., a solution of 47.1 g of 4-nitrobenzoyl chloride is added to 47.0 g of xylene. The resulting mixture is then heated to reflux for 1 h. The organic phase is cooled, and the reaction product precipitates. The product is recovered by filtration, washing with xylene and drying at 110° C. under vacuum, to obtain 83 g of yellow powder corresponding to 2-ethylhexyl 4-(4-nitrobenzamido) benzoate. The NMR spectrum and HPLC-MS analysis confirm the identity and molecular weight of the compound, the melting point of which is 105° C. (recrystallised from methanol).

Example 2: Synthesis of 2-ethylhexyl 4-(4-aminobenzamido) benzoate 210.0 g of xylene, 70.1 g of compound obtained according to Example 1 and 0.70 g of 5% Pd/C catalyst (50% solution in water) are loaded into a 1 L steel autoclave. The mixture is decontaminated with nitrogen and hydrogenated, operating at a pressure of 10 bars with hydrogen at 90° C. The xylene solution is filtered hot through a Buchner funnel heated to 90° C. to remove the catalyst. The clear solution is left to cool, and the product precipitates. The precipitate is filtered through a Buchner funnel, and the panel is washed with xylene and dried in a vacuum oven at 110° C. About 64 g of product is obtained as a whitish powder. The NMR spectrum and HPLC-MS analysis confirm the identity and molecular weight of the compound, the melting point of which is 137° C. (recrystallised from toluene).

Example 3: Synthesis of 4-[(4,6-dichloro-1,3,5-triazine-2-yl)amino]-N-(1,1-dimethylethyl)benzamide 17.6 g of sodium bicarbonate is added under stirring to a solution of 37 g of cyanuryl chloride in 450 ml of acetone, cooled to 0° C., then 39 g of N-tert-butyl 4-aminobenzamide is added slowly, always maintaining the temperature at 0° C. by cooling. The mixture is then maintained under stirring for 30 minutes, after which 150 ml of water is added, followed by stirring for a further 30 minutes. The precipitate that forms is filtered, washed several times with water and dried under vacuum. 64 g of dichlorotriazine derivative is obtained as a white powder with a melting point >250° C.

Example 4: Synthesis of the Compound of Formula (V)

10.2 g of the compound of Example 3 (dichlorotriazine derivative) and 22.6 g of the compound of Example 2 in 200 ml of xylene are stirred at 140° C. to reflux and then treated with 100.0 g of 2.4 wt % aqueous sodium hydroxide. The water and solvent are eliminated by distillation under vacuum. The residue is taken up with 250 ml of acetone. The acetone solution is clarified by filtration, and the acetone is removed by distillation under vacuum. 30 g of a whitish solid corresponding to the compound of formula (V) is obtained. The NMR spectrum and HPLC-MS analysis confirm the identity and molecular weight of the compound, the melting point of which is 232° C.

Example 5: Synthesis of 2-ethylhexyl 4-((4-(4-(tert-butylcarbamoyl)-phenylamino)-6-chloro-1,3,5-triazine-2-yl)amino)benzoate 51 g of the compound of Example 3 is reacted with 38.1 g of 2-ethylhexyl-4-aminobenzoate in the presence of 59.6 g of triisobutylamine in 200 ml of toluene at 110° C. for 3 hours. The mass is cooled and diluted with 100 ml of toluene. 200 ml of water and 16.3 g of concentrated hydrochloric acid are then added under stirring. The aqueous phase is separated and eliminated. The organic phase is washed with water and then filtered. The solid is suspended in n-hexane and recovered by filtration and drying. 68.4 g of white solid with a melting point of 166° C. is obtained.

Example 6: Synthesis of the Compound of Formula (VI)

16.6 g of compound obtained according to Example 5 is reacted with 11.8 g of the compound of Example 2 in the presence of 55 g of 5 wt % aqueous solution of sodium carbonate, 4 g of 30% sodium hydroxide and 100 ml of xylene at reflux for 6 hours. The aqueous phase is separated and eliminated hot. The organic phase is dried by azeotropic distillation, and clarified by hot filtration. The precipitate is cooled and recovered by filtration, washing and drying, and 26.4 g of crude product is obtained. This compound is purified by crystallisation from toluene and methylcyclohexane. 20 g of a white product with a melting point of 118° C. is obtained.

Example 7: Synthesis of 2-ethylhexyl N-(4-((4,6-dichloro-1,3,5-triazine-2-yl)amino)benzoyl)-4-aminobenzoate 38.7 g of the compound of Example 2, namely 2-ethylhexyl 4-(4-aminobenzamido)benzoate, is gradually added to a stirred mixture of 18.5 g of cyanuryl chloride, 200 ml of acetone and 9.3 g of sodium bicarbonate maintained at −5° C. The mixture is left to react for one hour at 0° C., and 80 g of water is then added. The solid precipitate is filtered and washed with water and 5% acetone. The filtrate is dried at 40° C. under vacuum. 49.2 g of a whitish solid with a melting point of 250° C. and 13.61 wt % Cl is obtained (theoretical value 13.76 wt % Cl).

Example 8: Synthesis of the Compound of Formula (VII)

15.5 g of the compound of Example 7 and 15.3 g of 2-ethylhexyl 4-aminobenzoate are reacted under stirring in 200 ml of xylene at reflux, gradually adding 100.0 g of 2.4 wt % aqueous sodium hydroxide. The water is eliminated by azeotropic distillation. The xylene solution is filtered hot to clarify it. When the solution is cooled, a precipitate forms which is washed with cold xylene and dried at 60° C. under vacuum. 23 g of a white crystalline solid with a melting point of 146° C. is obtained. The NMR spectrum confirms the identity of the compound obtained.

Example 9—Application

The compounds of formulas (V), (VI) and (VII) were tested for their ability to perform a photoprotective action. Said compounds were added to standard cosmetic formulas (formulas shown in Table 1) to evaluate the SPF (sun protection factor) value with a Labsphere UV-2000S instrument in the UV-visible region from 290 to 400 nm. For the experimental measurement of the SPF, the cosmetic formula was applied to a Transpore medium (3M Inc.) at a concentration of 2.0 mg/cm$^2$. 3 tapes were prepared for each formula, 12 readings per tape being conducted; readings with a covariance >10% above the average were rejected. The SPF data are set out in Table 2.

TABLE 1

| Phase | Ingredient | INCI name | Formula 1 | Formula 2 | Formula 2 |
|---|---|---|---|---|---|
| A1 | Water | water | 72.5 | 72.5 | 72.5 |
| A1 | Propylene Glycol | propylene glycol | 1 | 1 | 1 |
| A2 | Satiaxane CX91 | xanthan gum | 0.6 | 0.6 | 0.6 |
| A2 | Ultrez 10 | Carbomer | 0.15 | 0.15 | 0.15 |
| A2 | Disodium EDTA | disodium EDTA | 0.08 | 0.08 | 0.08 |
| B1 | Lanette 16 | cetyl alcohol | 1 | 1 | 1 |
| B1 | Tego alkanol S21P | steareth-21 | 2.5 | 2.5 | 2.5 |

TABLE 1-continued

| Phase | Ingredient | INCI name | Formula 1 | Formula 2 | Formula 2 |
|---|---|---|---|---|---|
| B1 | Tego alkanol S2P | steareth-2 | 3 | 3 | 3 |
| B1 | Cetiol CC | dicaprylyl carbonate | 6.5 | 6.5 | 6.5 |
| B1 | Tegosoft DC | decyl cocoate | 6.5 | 6.5 | 6.5 |
| B2 | Compound of formula (V) | | 1 | | |
| B2 | Compound of formula (VI) | | | 1 | |
| B2 | Compound of formula (VII) | | | | 1 |
| C | TEA | TEA | 0.225 | 0.225 | 0.225 |
| D | Dow Corning 245 | cyclomethicone | 2 | 2 | 2 |
| D | Microcare PMS | phenoxyethanol and paraben | 1 | 1 | 1 |

Preparation: Phase B1 was heated to 70°–75° C. under stirring, and B2 was then added. A1 was heated separately to 70°–75° C., adding phase A2 and homogenising with a turboemulsifier. Maintaining the temperature at 70°–75° C., B1+B2 was poured into A1, and homogenised with a turboemulsifier. After adding C, the formulation was cooled to 40° C., and phase D was then added, again under stirring.

TABLE 2

| Formula | Mean SPF | UVA:UVB ratio | Critical wavelength |
|---|---|---|---|
| 1 | 3.50 | 0.58 | 314.0 |
| 2 | 3.21 | 0.33 | 311.0 |
| 3 | 3.15 | 0.35 | 313.0 |

The UVA:UVB ratio is the ratio between the intensity of the radiation absorbed between 320 nm and 400 nm (UVA fraction) and that absorbed between 290 nm and 320 nm (UVB fraction). The UVA fraction of the compounds of formulas (V), (VI) and (VII) of the invention is at least twice as high as those of the triazine analogues already known, such as diethylhexyl butamido triazone and ethylhexyl triazone, for which said ratio is between 0.12 and 0.14.

The invention claimed is:

1. Triazine compounds of general formula (I):

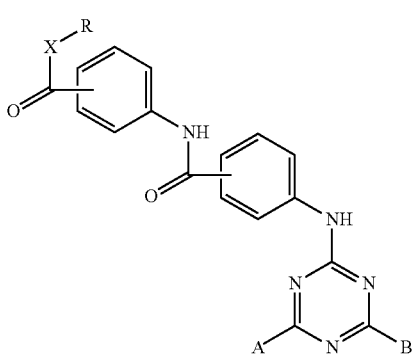

wherein:

X is an —O— or —NH— group,

R is a straight, cyclic or branched $C_1$-$C_{18}$ alkyl group, and the groups A and B can be, independently of one another:

a group of formula (II)

wherein $R_1$ and $R_2$ can be, independently of one another, H, straight, cyclic or branched $C_1$-$C_{22}$ alkyls or $C_1$-$C_{18}$ hydroxyalkyl or $C_2$-$C_{18}$ alkoxyalkyl, polyalkylene glycols or a group of formula (III)

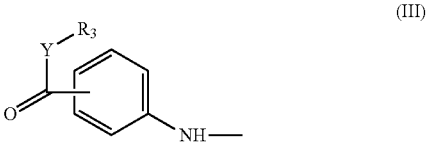

wherein Y, independently of the value di X, is a —O— or —NH— group $R_3$ is a straight, cyclic or branched $C_1$-$C_{18}$ alkyl group which is the same or different from R or a group of formula (IV)

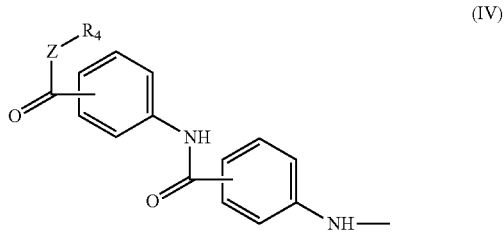

wherein Z, independently of the value of X and Y, is an —O— or —NH— group $R_4$ is a straight, cyclic or branched $C_1$-$C_{18}$ alkyl group which is the same or different from R and $R_3$.

2. Compounds of claim 1 wherein the carboxylate —CO—O— or amide —CO—NH— groups, or the —CO—X—, —CO—Y—, —CO—Z— groups on the phenyl rings are at the para, i.e. 4, position to the —NH— group and the groups R, $R_1$, $R_2$, $R_3$ and $R_4$ are alkyl straight or branched $C_1$-$C_{12}$ groups.

3. Compounds of claim 1 selected from the compounds of formula (V), (VI) and (VII):

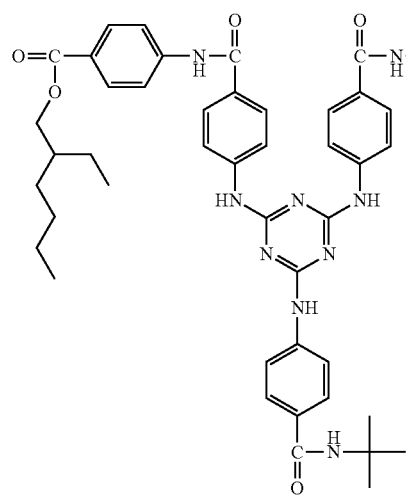

(V)

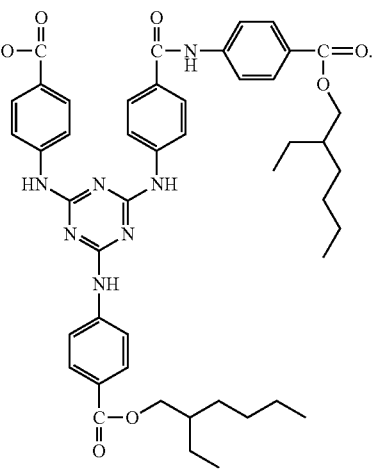

(VII)

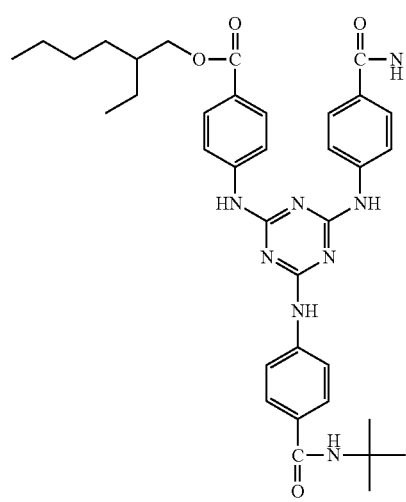

(VI)

4. Compounds of claim 1 having a UVA/UVB ratio greater than 0.20.

5. Cosmetic compositions containing the compounds of claim 1 alone or in mixture with one or more UVA and UVB sunscreens.

6. Cosmetic compositions of claim 5 containing also one or more sunscreens selected from: 2-ethylhexyl p-methoxycinnamate, 2-hydroxy-4-methoxybenzophenone, 2-hydroxy-4-methoxybenzophenone-5-sulfonic acid, ethylhexyl salicylate, ethylhexyl dimethyl PABA, drometrizole trisiloxane, 3-(4'-methylbenzylidene)-d,l-camphor, Dietilhexyl Butamido Triazone, Ethylhexyl Triazone, 4-(tert-butyl)-4'-methoxy-dibenzoylmethane, 2-ethylhexyl ester of 2-cyano-3,3-diphenylacrylic acid, bis-ethylhexyloxyphenol-methoxyphenyl-triazine, methylene-bis-benzotriazolyl-tetramethylbutylphenol, 2-(4-diethylamino-2-hydroxybenzoyl)-hexyl ester of benzoic acid, 2,4-bis-[4-[5-(1,1-dimethyl-propyl)benzoxazol-2-yl]phenylimino]-6-[(2-ethylhexyl)imino]-1,3,5-triazine, tris-biphenyltriazine, titanium dioxide and zinc oxide.

* * * * *